United States Patent
Chen et al.

(10) Patent No.: US 10,258,577 B2
(45) Date of Patent: Apr. 16, 2019

(54) MULTILAYER SOLID PHARMACEUTICAL DOSAGE FORMS

(71) Applicant: NOVAST LABORATORIES LTD, Jiangsu (CN)

(72) Inventors: Yisheng Chen, Jiangsu (CN); Guohua Zhang, Jiangsu (CN); Manman Liu, Jiangsu (CN)

(73) Assignee: NOVAST LABORATORIES LTD, Jiangsu (CN)

( * ) Notice: Subject to any disclaimer, the term of this patent is extended or adjusted under 35 U.S.C. 154(b) by 0 days.

(21) Appl. No.: 15/037,314

(22) PCT Filed: Jun. 16, 2014

(86) PCT No.: PCT/CN2014/079956
§ 371 (c)(1),
(2) Date: May 17, 2016

(87) PCT Pub. No.: WO2015/085739
PCT Pub. Date: Jun. 18, 2015

(65) Prior Publication Data
US 2016/0287520 A1    Oct. 6, 2016

(30) Foreign Application Priority Data

Dec. 12, 2013    (CN) .......................... 2013 1 0673039

(51) Int. Cl.
| | |
|---|---|
| *A61K 9/28* | (2006.01) |
| *A61K 31/138* | (2006.01) |
| *A61K 31/155* | (2006.01) |
| *A61K 31/554* | (2006.01) |
| *A61K 9/24* | (2006.01) |
| *A61K 9/50* | (2006.01) |
| *A61K 9/20* | (2006.01) |

(52) U.S. Cl.
CPC ............ *A61K 9/2886* (2013.01); *A61K 9/209* (2013.01); *A61K 9/2013* (2013.01); *A61K 9/2027* (2013.01); *A61K 9/2054* (2013.01); *A61K 9/282* (2013.01); *A61K 9/2813* (2013.01); *A61K 9/2846* (2013.01); *A61K 9/5073* (2013.01); *A61K 31/138* (2013.01); *A61K 31/155* (2013.01); *A61K 31/554* (2013.01)

(58) Field of Classification Search
CPC .... A61K 9/209; A61K 9/2846; A61K 9/2886; A61K 9/5073
See application file for complete search history.

(56) References Cited

U.S. PATENT DOCUMENTS

| | | | |
|---|---|---|---|
| 2003/0180352 A1* | 9/2003 | Patel .................... | A61K 9/1617 424/465 |
| 2006/0269605 A1* | 11/2006 | Lizio .................... | A61K 9/5078 424/472 |

FOREIGN PATENT DOCUMENTS

CN    101143140    3/2008

OTHER PUBLICATIONS

Kilicarslan et al, J. Microencapsulation, Mar. 2004, vol. 21, No. 2, pp. 175-189.*
"International Search Report (Form PCT/ISA/210)", dated Sep. 24, 2014, with English translation thereof, pp. 1-4.

* cited by examiner

*Primary Examiner* — Kyle A Purdy
(74) *Attorney, Agent, or Firm* — JCIPRNET

(57) ABSTRACT

Disclosed is a multilayer solid pharmaceutical dosage form, wherein a core containing an active ingredient is coated with a first sustained-release coating layer, a drug layer containing the active ingredient is applied onto the first layer, and a second sustained-release coating layer is applied onto the drug layer.

23 Claims, 3 Drawing Sheets

MULTILAYER SOLID PHARMACEUTICAL DOSAGE FORMS

CROSS-REFERENCE TO RELATED APPLICATION

This application is a 371 application of an International PCT application serial no. PCT/CN2014/079956, filed on Jun. 16, 2014, which claims the priority benefit of China application serial no. 201310673039.5, filed on Dec. 12, 2013. The entirety of each of the above-mentioned patent applications is hereby incorporated by reference herein and made a part of this specification.

BACKGROUND OF THE INVENTION

Field of the Invention

The present invention relates to a multilayer solid pharmaceutical sustained-release dosage form.

Description of Related Art

Pharmaceutical formulation science has made significant advances over the previous 20 years. However, with each advance comes additional information demonstrating various shortfalls in pharmaceutical formulations. A pharmaceutical scientist desires to have precision relating to the release profile of a particular active ingredient in vivo. Various physical and chemical environments present unique challenges relating to formulation of a desired release profile. The present invention addresses the desire to control the release profile by providing a multilayer dosage form in which drug release is more precisely controlled.

SUMMARY OF THE INVENTION

An objective of the present invention is, in order to overcome the above drawbacks, to provide a multilayer solid pharmaceutical sustained-release dosage form, by which the problem of drug release after a lag time is solved.

Technical solutions of the present invention are as follow:

A multilayer solid pharmaceutical dosage form comprising:

a core containing a portion of an active pharmaceutical ingredient;

a first permeable and insoluble coating layer covering the core;

a drug layer containing a portion of the active ingredient covering the first permeable and insoluble coating layer; and a second permeable and insoluble coating layer covering the drug layer.

According to a further improvement of the present invention, the core is a tablet.

According to a further improvement of the present invention, the core is a pellet.

According to a further improvement of the present invention, the first permeable and insoluble coating layer and/or the second permeable and insoluble coating layer contains a mixture of methacrylate copolymer materials, wherein the first material is a high-permeability pH-independent swellable methacrylate copolymer, and the second material is a low-permeability pH-independent swellable methacrylate copolymer, the ratio of the first and second methacrylate copolymers is 4:1-1:4.

According to a further improvement of the present invention, the ratio of the first and second methacrylate copolymers is 3:1-1:3.

According to a further improvement of the present invention, the first methacrylate copolymer is a copolymer of ethyl acrylate:methyl methacrylate. trimethylammonioethyl methacrylate chloride=1:2:0.2, with a weight average molar mass of about 32,000 g/mol, and the second methacrylate copolymer is a copolymer of ethyl acrylate:methyl methacrylate:trimethylammonioethyl methacrylate chloride=1:2:0.1, with a weight average molar mass of about 32,000 g/mol.

According to a further improvement of the present invention, the first permeable and insoluble coating layer and/or the second permeable and insoluble coating layer contains ethyl cellulose.

According to a further improvement of the present invention, the drug layer containing a portion of the active pharmaceutical ingredient contains a binder.

According to a further improvement of the present invention, the binder is selected from starch, gelatin, zein, guar gum, hydroxyethyl cellulose, methyl cellulose, poloxamers, polyethylene oxide, polyvinyl pyrrolidone, hydroxypropyl cellulose, hydroxypropylmethyl cellulose, microcrystalline cellulose, and any combination thereof.

According to a further improvement of the present invention, the active pharmaceutical ingredient is a drug for the treatment of diabetes, cardiovascular diseases, or central nervous system diseases, including metformin and/or a salt thereof, metoprolol and/or a salt thereof, and diltiazem and/or a salt thereof.

A multilayer solid pharmaceutical dosage form comprising:

a seal-coated core containing a portion of an active pharmaceutical ingredient;

a first permeable and insoluble coating layer covering the seal-coated core;

a drug layer containing a portion of the active ingredient covering the first permeable and insoluble coating layer;

a second permeable and insoluble coating layer covering the drug layer; and optionally, a seal coating layer between the drug layer and the permeable and insoluble coating layers.

According to a further improvement of the present invention, the seal-coated core is a tablet.

According to a further improvement of the present invention, the seal-coated core is a pellet.

According to a further improvement of the present invention, the seal-coated core comprises a core coated with a layer of a water-soluble polymer.

According to a further improvement of the present invention, the first permeable and insoluble coating layer and/or the second permeable and insoluble coating layer contains a mixture of methacrylate copolymer materials, wherein the first material is a high-permeability pH-independent swellable methacrylate copolymer, and the second material is a low-permeability pH-independent swellable methacrylate copolymer, wherein the ratio of the first and second methacrylate copolymers is 4:1-1:4.

According to a further improvement of the present invention, the ratio of the first and second methacrylate copolymers is 3:1-1:3.

According to a further improvement of the present invention, the first methacrylate copolymer is a copolymer of ethyl acrylate:methyl methacrylate:trimethylammonioethyl methacrylate chloride=1:2:0.2, with a weight average molar mass of about 32,000 g/mol, and the second methacrylate copolymer is a copolymer of ethyl acrylate:methyl methacrylate:trimethylammonioethyl methacrylate chloride=1:2:0.1, with a weight average molar mass of about 32,000 g/mol.

According to a further improvement of the present invention, the first permeable and insoluble coating layer and/or the second permeable and insoluble coating layer contains ethyl cellulose.

According to a further improvement of the present invention, the drug layer containing a portion of the active pharmaceutical ingredient contains a binder.

According to a further improvement of the present invention, the binder is selected from starch, gelatin, zein, guar gum, hydroxyethyl cellulose, methyl cellulose, poloxamers, polyethylene oxide, polyvinyl pyrrolidone, hydroxypropyl cellulose, hydroxypropylmethyl cellulose, microcrystalline cellulose, and any mixture thereof.

According to a further improvement of the present invention, the active pharmaceutical ingredient is a drug for the treatment of diabetes, cardiovascular diseases, or central nervous system diseases, including metformin and/or a salt thereof, metoprolol and/or a salt thereof, and diltiazem and/or a salt thereof.

Compared with the prior art, the present invention has the following advantages in that: the present invention aims to design a new sustained-release dosage form in the field of pharmaceutics. It is difficult to achieve the desired drug release profile with conventional single-layer film control technology. The unique formulation and configurations of the present invention form a drug delivery system in which the active ingredient comes from each coating layer and the core, hence the delivery rate can be more precisely designed and controlled. According to the present invention, formulation scientists can design a solid dosage form to provide a variety of different release profiles for the active ingredient to achieve a desired sustained-release profile, and a precise control of drug delivery rate, meeting the needs of medication.

DETAILED DESCRIPTION OF THE INVENTION

Figure 1:
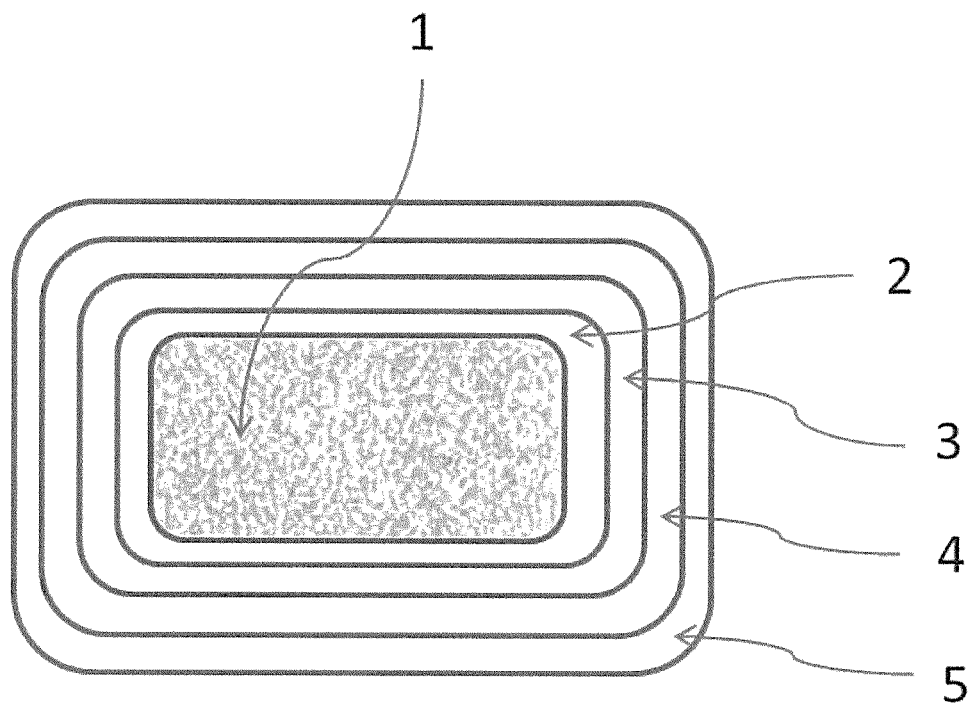
FIG. 1 is a schematic view of a structure according to the present invention.

In order to enhance the understanding of the invention, the present invention will be further described in detail below in conjunction with examples and drawings. The following examples are intended for illustration only and should not be construed as limitations for the scope of the present invention.

A multilayer solid pharmaceutical dosage form, comprising
a core 1 containing a portion of an active pharmaceutical ingredient;
a first permeable and insoluble coating layer 2 covering the core 1;
a drug layer 3 containing a portion of the active ingredient covering the first permeable and insoluble coating layer 2; and
a second permeable and insoluble coating layer 4 covering the drug layer 3.

The core 1 is a tablet or a pellet. The first permeable and insoluble coating layer 2 and/or the second permeable and insoluble coating layer 4 contains a mixture of methacrylate copolymer materials, wherein the first material is a high-permeability pH-independent swellable methacrylate copolymer; and the second material is a low-permeability pH-independent swellable material, wherein the ratio of the first and second methacrylate copolymers is 4:1-1:4. Wherein in a further improvement, the ratio of the first and second methacrylate copolymers is 3:1-1:3. The first methacrylate copolymer is a copolymer of ethyl acrylate:methyl methacrylate:trimethylammonioethyl methacrylate chloride=1:2:0.2, with a weight average molar mass of about 32,000 g/mol, and the second methacrylate copolymer is a copolymer of ethyl acrylate:methyl methacrylate:trimethylammonioethyl methacrylate chloride=1:2:0.1, with a weight average molar mass of about 32,000 g/mol. The first permeable and insoluble coating layer 2 and/or the second permeable and insoluble coating layer 4 contains ethyl cellulose. The drug layer 3 containing a portion of the active pharmaceutical ingredient contains a binder. The binder is selected from starch, gelatin, zein, guar gum, hydroxyethyl cellulose, methyl cellulose, poloxamers, polyethylene oxide, polyvinyl pyrrolidone, hydroxypropyl cellulose, hydroxypropylmethyl cellulose, microcrystalline cellulose, and any combination thereof. The active pharmaceutical ingredient is a drug for the treatment of diabetes, cardiovascular diseases, or central nervous system diseases, including metformin and/or a salt thereof, metoprolol and/or a salt thereof, and diltiazem and/or a salt thereof.

A multilayer solid pharmaceutical dosage form, comprising:
a seal-coated core 1 containing a portion of an active pharmaceutical ingredient;
a first permeable and insoluble coating layer 2 covering the seal-coated core 1;
a drug layer 3 containing a portion of the active ingredient covering the first permeable and insoluble coating layer 2;
a second permeable and insoluble coating layer 4 covering the drug layer 3; and
optionally, an seal coating layer between the drug layer 3 and the permeable and insoluble coating layers 2, 4.

The seal coated core 1 is a tablet or a pellet. The seal coated core 1 comprises a core coated with a layer of a water-soluble polymer. The first permeable and insoluble coating layer and/or the second permeable and insoluble coating layer contains a mixture of methacrylate copolymer materials, wherein the first material is a high-permeability pH-independent swellable methacrylate copolymer, and the second material is a low-permeability pH-independent swellable methacrylate copolymer, wherein the ratio of the first and second methacrylate copolymers is 4:1-1:4. Wherein the ratio of the first and second methacrylate copolymers is 3:1-1:3. The first methacrylate copolymer is a copolymer of ethyl acrylate:methyl methacrylate:trimethylammonioethyl methacrylate chloride=1:2:0.2, with a weight average molar mass of about 32,000 g/mol, and the second methacrylate copolymer is a copolymer of ethyl acrylate:methyl methacrylate:trimethylammonioethyl methacrylate chloride=1:2:0.1, with a weight average molar mass of about 32,000 g/mol. The first permeable and insoluble coating layer 2 and/or the second permeable and insoluble coating layer 4 contains ethyl cellulose. The drug layer 3 containing a portion of the active pharmaceutical ingredient contains a binder. The binder is selected from starch, gelatin, zein, guar gum, hydroxyethyl cellulose, methyl cellulose, poloxamers, polyethylene oxide, polyvinyl pyrrolidone, hydroxypropyl cellulose, hydroxypropylmethyl cellulose, microcrystalline cellulose, and any mixture thereof. The active pharmaceutical ingredient is a drug for the treatment of diabetes, cardiovascular diseases, or central nervous system diseases, including metformin, metoprolol, diltiazem, or salts thereof.

In a preferred embodiment, the core contains a portion of a therapeutic dose of the active pharmaceutical ingredient and pharmaceutical excipients. The active pharmaceutical ingredient referred to herein is a pharmaceutical compound or a salt thereof. The active pharmaceutical ingredient may be mixed with the excipients and processed into a pellet or compressed into a tablet core according to methods known in the art.

In a specific embodiment, the core contains a binder.

Suitable binders known in the art include, but are not limited to, starch, gelatin, zein, guar gum, methyl cellulose, poloxamers, polyethylene oxide, polyvinyl pyrrolidone, hydroxypropyl cellulose, hydroxypropylmethyl cellulose, hydroxyethyl cellulose, microcrystalline cellulose, and any combination thereof.

In a specific embodiment, the core uses a mixture of hydroxypropyl cellulose and polyvinyl pyrrolidone as a binder.

In a preferred specific embodiment, the core is coated with the first permeable and insoluble coating film to adjust the release rate of the drug from the core.

The core may be coated with one or more layers of enteric coating, or seal coating, or barrier coating by coating techniques such as film coating or compression coating. For the intended purpose, a multilayer coating may be used. Further, the core may be designed with any of the immediate-release, controlled-release, sustained-release, or targeted delayed-release to achieve the desired performance. The definitions of these terms are apparent to those skilled in the art. Furthermore, the release profile of a formulation may also be affected by the types of formulation components and levels thereof.

The coating can be applied to tablets (molded or compressed tablets), capsules, mini-pills, pellets, beads, granules, or powders. The coating can be achieved by the use of an aqueous dispersion of a coating material or a solution formed by dissolving a coating material in a suitable solvent. Other additives and levels thereof as well as the main coating materials will be selected depending on the specific needs for each product.

The coating layers typically may also contain a plasticizer, as well as other coating excipients such as a coloring agent, talc, or magnesium stearate, which are well known by those skilled in the art. Suitable plasticizers include: triethyl citrate, glycerol triacetate, acetyl triethyl citrate, polyethylene glycol, diethyl phthalate, tributyl citrate, acetylated monoglyceride, glycerol, fatty acid esters, propylene glycol, and dibutyl phthalate, and the like. Specifically, the methacrylate copolymer coatings typically contain 10 to 25% by weight of a plasticizer, especially dibutyl phthalate, polyethylene glycol, triethyl citrate, or acetyl triethyl citrate. The present invention adopts a conventional coating technique such as pan-spray coating for coating. The present invention also contemplates the use of a fluidized bed spray coating for tablet coating.

In addition to a plasticizer for solubilizing or dispersing a coating material, a penetration enhancer, a coloring agent, an antisticking agent, a surfactant, a defoamer, a lubricant, a stabilizer, and the like may also be added into the coating layers, to improve the coating process and product performance.

The coating process often involves spraying a coating solution onto a substrate. The coating solution may be a molten liquid of coating ingredients free of a dispersion medium, and may also be a solution formed by dissolving or suspending the coating ingredients in an aqueous medium, an organic solvent, or a mixture thereof. Upon the completion of the coating, the residual dispersion medium can be removed by using a suitable drying process, such as vacuum evaporation, heating, or a method with a drying air flow without heating, to reach a desired level.

A solvent-based coating means that coating ingredients are dissolved or dispersed in an organic solvent. Preferably, the boiling point and evaporation coefficient of the solvent are both lower than that of water. In order to obtain suitable viscosity and solubilization effect, a mixed organic solvent or a mixed solvent of water and an organic solvent is often used. Typical solvents include ethanol, methanol, isopropyl alcohol, acetone, dichloromethane, trichloromethane, and ethyl acetate, and the like. A suitable polymer may be added as required. A cellulose derivative and a polymethacrylate are particularly suitable for a solvent-based coating. Stirring or heating can promote dissolution and solubilization processes of the coating material. A plasticizer may also be added to promote dissolution. A coloring agent and an antisticking agent may also be used as required.

The following examples further exemplify the invention and are not intended to limit the scope of the present invention.

A general scheme is described as follows:

In a preferred specific embodiment, a tablet core is covered with a first film layer. With methods known in the art, the covering comprises a partial coverage or a complete coverage of the tablet. In a specific embodiment, the tablet core is completely covered with a material forming a permeable coating film. In a preferred specific embodiment, the permeable coating film is formed from a component which can control the release of an active pharmaceutical ingredient from the tablet core.

In another preferred specific embodiment, the first permeable and insoluble coating layer contains a mixture of methacrylate copolymer materials, wherein the first material is a high-permeability pH-independent swellable methacrylate copolymer; and the second material is a low-permeability pH-independent swellable methacrylate copolymer. In this non-limiting example, a preferred mixture is formed by mixing Eudragit® RL and Eudragit® RS. In a preferred embodiment, the ratio of Eudragit® RL and Eudragit® RS is 4:1-1:4. In another preferred specific embodiment, the ratio of Eudragit® RL and Eudragit® RS is 3:1-1:3.

Eudragit® RL and Eudragit® RS are insoluble and permeable polymers, having a pH-independent swellable property. Eudragit® RL has a high permeability, and Eudragit® RS has a low permeability. Thus, the two polymers are used to assess coating of a metformin hydrochloride (MFH) tablet. A screening study was performed by using mixtures of the two polymers of Eudragit® RL and Eudragit® RS at a ratio of 4:1, 1:1 and 1:4 in the formulas for coating. Immediate-release (IR) tablet cores were coated with these respective formulas, forming the corresponding layers of continuous coating film having the same theoretical weight gain. The compositions of the coated tablets are shown in Table 1.

Figure 2:
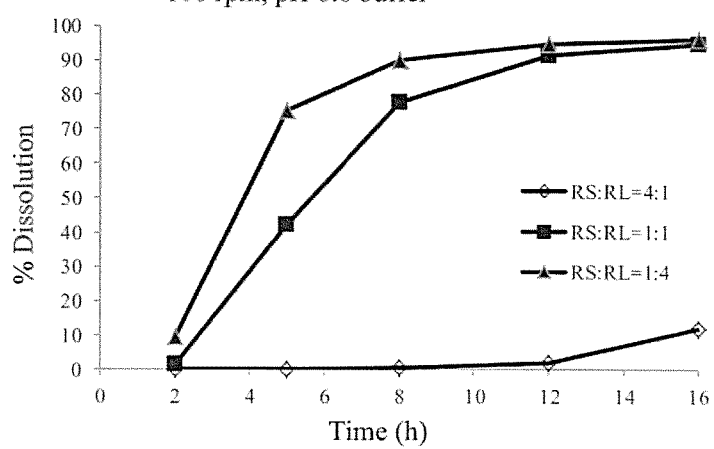
FIG. 2 is a graph showing the dissolution results of a single-layer coated tablet.

As listed in Table 1, the coating films contain Eudragit® RL and Eudragit® RS as polymers for controlling the release rate, triethyl citrate as a plasticizer, and talc as an antisticking agent. The dissolution results of the resulting single-layer coated tablets are shown in FIG. 2. The dissolution results in this figure show that the coating films are permeable to the drug, and using different ratios of Eudragit® RL and Eudragit® RS in the single-layer coating films can provide a wide range of dissolution profiles, but there is a deficiency with a significant lag time in release.

TABLE 1

Formulas for screening of single-layer coating

| Ingredient | Composition (mg/tablet) | | |
|---|---|---|---|
| Tablet core | | | |
| Metformin hydrochloride | 1000 | 1000 | 1000 |
| Polyvinyl pyrrolidone | 63.8 | 63.8 | 63.8 |
| Hydroxypropyl cellulose | 68.3 | 68.3 | 68.3 |
| Purified water[a] | q.s. | q.s. | q.s. |
| Magnesium stearate | 5.7 | 5.7 | 5.7 |
| Coating layer | | | |
| Eudragit ® RS | 53.6 | 33.5 | 13.4 |
| Eudragit ® RL | 13.4 | 33.5 | 53.6 |
| Triethyl citrate | 13.4 | 13.4 | 13.4 |
| Talc | 33.5 | 33.5 | 33.5 |
| 95% Ethanol[a] | q.s. | q.s. | q.s. |

[a]solvent, removed during process.

Figure 3:
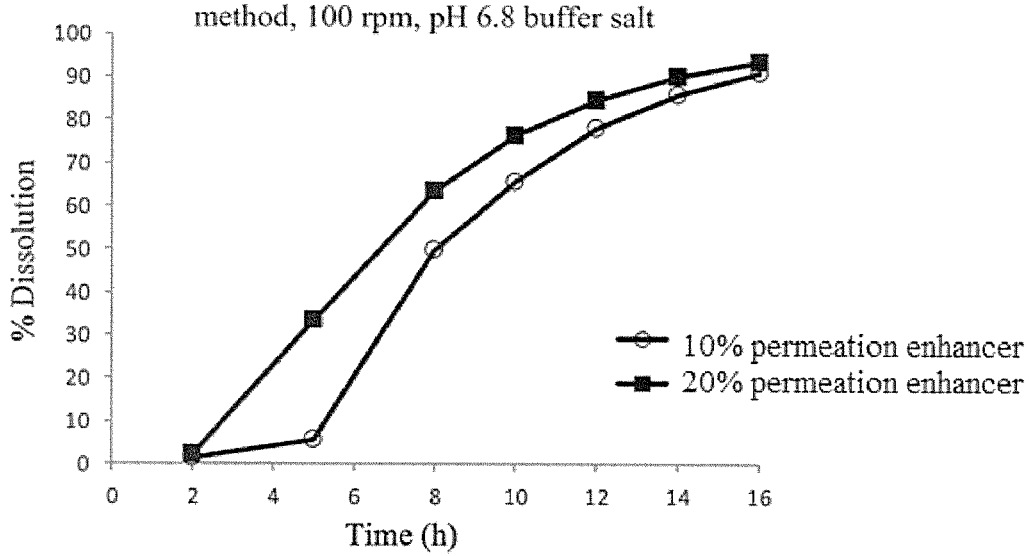
FIG. 3 is a dissolution profile of a single-layer coated tablet.

Based on the results of the above-mentioned screening study, the ratio of Eudragit® RS and Eudragit® RL in the single-layer coating formula was adjusted, and metformin hydrochloride was used as a permeation enhancer. As listed in Table 2, two levels of metformin hydrochloride were respectively used in the coating layer. The dissolution profiles of the resulting single-layer coated tablets are shown in FIG. 3. The addition of metformin hydrochloride in the coating layer promotes the release rate of the drug from the coated tablets. However, it is obvious that coating of a single layer of rate controlling polymer resulted in a lag time in drug release, which is clearly not desired.

TABLE 2

Formulas for single-layer coating of metformin hydrochloride sustained release tablets, 1000 mg

| Ingredient | Composition (mg/tablet) | |
|---|---|---|
| Tablet core | | |
| Core tablet of metformin hydrochloride | 1137.8 | 1137.8 |
| Sustained-release coating layer | | |
| Eudragit ® RS | 42.1 | 39.9 |
| Eudragit ® RL | 21.1 | 20.0 |
| Triethyl citrate | 12.6 | 12.0 |
| Talc | 31.7 | 30.0 |
| Metformin hydrochloride | 6.4 | 12.0 |
| Purified water[a] | q.s. | q.s. |
| 95% Ethanol[a] | q.s. | q.s. |

[a]solvent, removed in during process.

Using the above tablets, the present invention creates a new sustained-release formulation. The present invention uses a multilayer coating technique to prepare a dosage form for regulating the release profile of a drug from a coated unit such as a tablet or a pellet. This new technique can effectively reduce the problem of the lag time in drug release which is common to conventional single-layer coated tablets or pellets. A preferred dissolution profile can be easily realized by using this new technique. A dosage form prepared with this technique comprises at least a unit comprising:

a core containing a portion of a therapeutic amount of a drug and pharmaceutical excipients;

a first coating film covering the core, wherein the coating film is a sustained-release permeable film containing water-insoluble polymers, a plasticizer, a permeation enhancer, and other excipients;

a drug layer covering the first sustained-release permeable film, wherein the drug layer contains a portion of the therapeutic amount of the drug, a binder, and other pharmaceutical excipients;

a second coating film covering the drug layer, wherein the coating film is a sustained-release permeable film containing water-insoluble polymers, a plasticizer, a permeation enhancer, and other excipients; and optionally, a non-controlled-release colored coating layer on the outer surface of the tablet.

Figure 4:
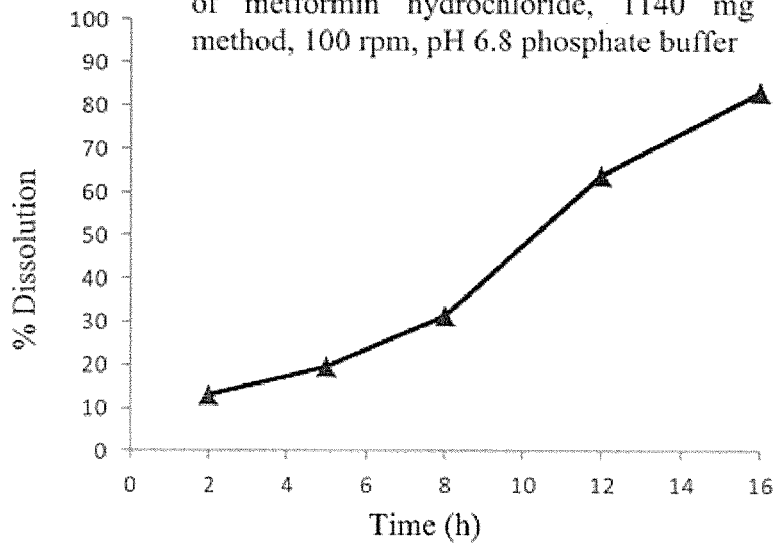
FIG. 4 is a graph showing the dissolution results of a multilayer sustained-release tablet.

In one embodiment, a prototype formulation for preparing a sustained-release tablet of metformin hydrochloride using a multilayer coating on an immediate-release tablet core is shown in Table 3. The tablet core and the drug layer of the tablet contain polyvinyl pyrrolidone, hydroxypropyl cellulose, and hydroxypropylmethyl cellulose. In the first and second layers of coating film, Eudragit® RL and Eudragit® RS are permeable and water-insoluble sustained-release polymers, triethyl citrate is a plasticizer, and metformin hydrochloride is a permeation enhancer. The immediate-release tablet core is made by the steps of conventional high shear granulation, drying, milling, mixing, lubricating, and compression. The first coating film, the drug layer, and the second coating film are made by coating with a perforated coating pan. The dissolution results of the resulting prototype multilayer sustained-release tablet are shown in FIG. 4. The dissolution profile in the figure shows that with the new technique of multilayer coating of the present invention, the problem of the lag time in drug release has been substantially minimized, while achieving the desired sustained-release purpose.

Figure 5:
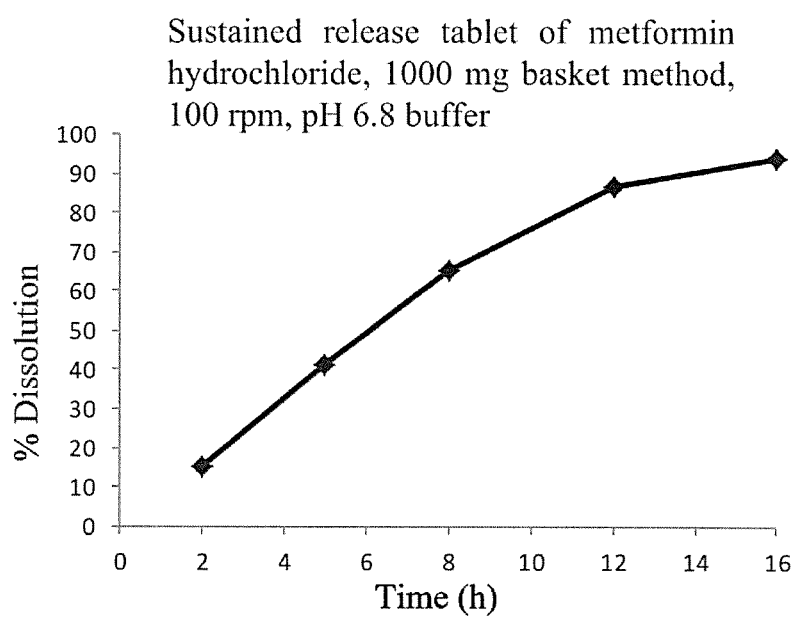
FIG. 5 is a dissolution profile of a multilayer sustained-release tablet of metformin hydrochloride;
the second permeable film coating, 5-colored coating.

Table 4 shows an example of a preferred composition of a multilayer sustained-release tablet of metformin hydrochloride. The dissolution profile of the resulting tablet is shown in FIG. 5. As can be seen, the multilayer coated dosage form of the present invention can effectively achieve the purpose of controlling drug release slowly without the lag time.

TABLE 3

Components of a prototype multilayer coated sustained-release tablet of metformin hydrochloride

| Ingredient | Composition (mg/tablet) |
|---|---|
| Tablet core | |
| Metformin hydrochloride | 900 |
| Polyvinyl pyrrolidone | 57.4 |
| Hydroxypropyl cellulose | 61.4 |
| Purified water[a] | q.s. |
| Magnesium stearate | 5.1 |
| First film coating layer | |
| Eudragit ® RS | 19.43 |
| Eudragit ® RL | 13.02 |
| Triethyl citrate | 6.51 |

TABLE 3-continued

Components of a prototype multilayer coated sustained-release tablet of metformin hydrochloride

| Ingredient | Composition (mg/tablet) |
| --- | --- |
| Talc | 16.17 |
| Metformin hydrochloride | 6.51 |
| Purified water[a] | q.s. |
| 95% Ethanol[a] | q.s. |
| Drug coating layer | |
| Metformin hydrochloride | 225.0 |
| Hydroxypropylmethyl cellulose | 28.0 |
| Purified water[a] | q.s. |
| Second film coating layer | |
| Eudragit ® RS | 25.4 |
| Eudragit ® RL | 17.0 |
| Triethyl citrate | 8.51 |
| Talc | 21.10 |
| Metformin hydrochloride | 8.51 |
| Purified water[a] | q.s. |
| 95% Ethanol[a] | q.s. |

[a]solvent, removed during process.

TABLE 4

Composition of a multilayer coated sustained-release tablet of metformin hydrochloride

| Ingredient | Composition (mg/tablet) |
| --- | --- |
| Tablet core | |
| Metformin hydrochloride | 800 |
| Polyvinyl pyrrolidone | 88.9 |
| Hydroxypropyl cellulose | 57.0 |
| Purified water[a] | q.s. |
| Magnesium stearate | 4.8 |
| First film coating layer | |
| Eudragit ® RS | 12.5 |
| Eudragit ® RL | 12.5 |
| Triethyl citrate | 5.0 |
| Talc | 12.5 |
| Metformin hydrochloride | 5.0 |
| Purified water[a] | q.s. |
| 95% Ethanol[a] | q.s. |
| Drug coating layer | |
| Metformin hydrochloride | 188.63 |
| Hydroxypropylmethyl cellulose | 23.58 |
| Purified water[a] | q.s. |
| Second film coating layer | |
| Eudragit ® RS | 15.89 |
| Eudragit ® RL | 15.89 |
| Triethyl citrate | 6.36 |
| Talc | 15.89 |
| Metformin hydrochloride | 6.36 |
| Purified water[a] | q.s. |
| 95% Ethanol[a] | q.s. |

[a]solvent, removed during process.

As can be seen from the exemplary examples above, the present invention comprises a core containing an active ingredient;

a first functional coating film covering the core;

a drug layer containing the active ingredient covering the first functional coating film; and a second functional coating film covering the drug layer.

In another embodiment, the active ingredient is included in the first layer and second layer of the functional coating layers, as shown in tables 3 and 4.

The unique formulations and configurations of the present invention form a delivery system whereby the delivery rate of an active ingredient from the various layers and the core is more precisely controlled.

According to the present invention, a formulation scientist can design a solid dosage form to provide a variety of different release profiles for an active ingredient to achieve a desired sustained-release profile.

Although the present invention has been described in its preferred forms or embodiments with some degree of particularity, it is understood that the description is given only by way of example, and variations may be made in many details of formulation ingredients, construction, manufacture, and usage, including the combination and arrangement of parts, without departing from the spirit and scope of the invention.

The invention claimed is:

1. A multilayer solid pharmaceutical sustained-release dosage form, comprising:
   a core (1) containing a portion of an active pharmaceutical ingredient;
   a first permeable and insoluble coating layer (2) covering the core (1);
   a drug layer (3) containing a portion of the active pharmaceutical ingredient covering the first permeable and insoluble coating layer (2); and
   a second permeable and insoluble coating layer (4) covering the drug layer (3),
   wherein the drug layer (3) is sandwiched between the first permeable and insoluble coating layer (2) and the second permeable and insoluble coating layer (4),
   wherein each of the first permeable and insoluble coating layer (2) and the second permeable and insoluble coating layer (4) contains a mixture of a first methacrylate copolymer material and a second methacrylate copolymer material, wherein the first methacrylate copolymer material is a high-permeability pH-independent swellable first methacrylate copolymer, and the second methacrylate copolymer material is a low-permeability pH-independent swellable second methacrylate copolymer, and
   wherein the first methacrylate copolymer is a copolymer of ethyl acrylate:methyl methacrylate:trimethylammonioethyl methacrylate chloride=1:2:0.2, and the second methacrylate copolymer is a copolymer of ethyl acrylate:methyl methacrylate:trimethylammonioethyl methacrylate chloride=1:2:0.1.

2. The sustained-release dosage form of claim 1, wherein the core (1) is a tablet.

3. The sustained-release dosage form of claim 1, wherein the core (1) is a pellet.

4. The sustained-release dosage form of claim 1, wherein a ratio of the first and second methacrylate copolymers is 4:1-1:4.

5. The sustained-release dosage form of claim 4, wherein the ratio of the first and second methacrylate copolymers is 3:1-1:3.

6. The sustained-release dosage form of claim 4, wherein the first methacrylate copolymer has a weight average molar mass of about 32,000 g/mol, and the second methacrylate copolymer has a weight average molar mass of about 32,000 g/mol.

7. The sustained-release dosage form of claim 1, wherein the permeable and insoluble first coating layer (2) and/or the second permeable and insoluble coating layer (4) contains ethyl cellulose.

8. The sustained-release dosage form of claim 1, wherein the drug layer (3) containing a portion of the active pharmaceutical ingredient contains a binder.

9. The sustained-release dosage form of claim 8, wherein the binder is selected from a group consisting of starch, gelatin, zein, guar gum, hydroxyethyl cellulose, methyl cellulose, poloxamers, polyethylene oxide, polyvinyl pyrrolidone, hydroxypropyl cellulose, hydroxypropylmethyl cellulose, microcrystalline cellulose, and any combination thereof.

10. The sustained-release dosage form of claim 1, wherein the active pharmaceutical ingredient is a drug for the treatment of diabetes, cardiovascular diseases, or central nervous system diseases, and is selected from a group consisting of metformin and/or a salt thereof, metoprolol and/or a salt thereof, and diltiazem and/or a salt thereof.

11. A multilayer solid pharmaceutical sustained-release dosage form, comprising:
a core (1) having a seal-coated layer, containing a portion of an active pharmaceutical ingredient;
a first permeable and insoluble coating layer (2) covering the core (1) having a seal-coated layer;
a drug layer (3) containing a portion of the active pharmaceutical ingredient covering the first permeable and insoluble coating layer (2);
a second permeable and insoluble coating layer (4) covering the drug layer (3); and
optionally, a seal coating layer between the drug layer (3) and the permeable and insoluble coating layers (2, 4),
wherein the drug layer (3) is sandwiched between the first permeable and insoluble coating layer (2) and the second permeable and insoluble coating layer (4),
wherein each of the first permeable and insoluble coating layer (2) and the second permeable and insoluble coating layer (4) contains a mixture of a first methacrylate copolymer material and a second methacrylate copolymer material, wherein the first methacrylate copolymer material is a high-permeability pH-independent swellable first methacrylate copolymer, and the second methacrylate copolymer material is a low-permeability pH-independent swellable second methacrylate copolymer, and
wherein the first methacrylate copolymer is a copolymer of ethyl acrylate:methylmethacrylate:trimethylammonioethyl methacrylate chloride=1:2:0.2, and the second methacrylate copolymer is a copolymer of ethyl acrylate:methyl methacrylate:trimethylammonioethyl methacrylate chloride=1:2:0.1.

12. The sustained-release dosage form of claim 11, wherein the core (1) having a seal-coated layer is a tablet.

13. The sustained-release dosage form of claim 11, wherein the core (1) having a seal-coated layer is a pellet.

14. The sustained-release dosage form of claim 11, wherein the core (1) having a seal-coated layer comprises a core coated with a layer of a water-soluble polymer.

15. The sustained-release dosage form of claim 11, wherein a ratio of the first and second methacrylate copolymers is 4:1-1:4.

16. The sustained-release dosage form of claim 15, wherein the ratio of the first and second methacrylate copolymers is 3:1-1:3.

17. The sustained-release dosage form of claim 15, wherein has a weight average molar mass of about 32,000 g/mol, and the second methacrylate copolymer has a weight average molar mass of about 32,000 g/mol.

18. The sustained-release dosage form of claim 11, wherein the first permeable and insoluble coating layer (2) and/or the second permeable and insoluble coating layer (4) contains ethyl cellulose.

19. The sustained-release dosage form of claim 11, wherein the drug layer (3) containing a portion of the active pharmaceutical ingredient contains a binder.

20. The sustained-release dosage form of claim 19, wherein the binder is selected from a group consisting of starch, gelatin, zein, guar gum, hydroxyethyl cellulose, methyl cellulose, poloxamers, polyethylene oxide, polyvinyl pyrrolidone, hydroxypropyl cellulose, hydroxypropylmethyl cellulose, microcrystalline cellulose, and any mixture thereof.

21. The sustained-release dosage form of claim 11, wherein the active pharmaceutical ingredient is a drug for the treatment of diabetes, cardiovascular diseases, or central nervous system diseases, and is selected from a group consisting of metformin and/or a salt thereof, metoprolol and/or a salt thereof, and diltiazem and/or a salt thereof.

22. The sustained-release dosage form of claim 5, wherein the first methacrylate copolymer has a weight average molar mass of about 32,000 g/mol, and the second methacrylate copolymer has a weight average molar mass of about 32,000 g/mol.

23. The sustained-release dosage form of claim 16, wherein the first methacrylate copolymer has a weight average molar mass of about 32,000 g/mol, and the second methacrylate copolymer has a weight average molar mass of about 32,000 g/mol.

* * * * *